United States Patent [19]

Larrabee

[11] 4,157,780
[45] Jun. 12, 1979

[54] DISPOSABLE, ROTATABLE, STAR-SHAPED ENCLOSURE FOR USE WITH BLOOD WASHING APPARATUS

[75] Inventor: Edward W. Larrabee, Bronxville, N.Y.

[73] Assignee: Union Carbide Corporation, New York, N.Y.

[21] Appl. No.: 847,447

[22] Filed: Nov. 1, 1977

[51] Int. Cl.² ............................................. B04B 15/06
[52] U.S. Cl. ................................... 233/14 R; 233/27
[58] Field of Search .............. 233/1 R, 1 A, 1 D, 1 E, 233/2, 3, 14 R, 14 A, 16, 27, 28, 32, 34, 38, 40, 44

[56] References Cited

U.S. PATENT DOCUMENTS

| | | | |
|---|---|---|---|
| 3,244,363 | 4/1966 | Hein | 233/28 |
| 3,991,935 | 11/1976 | Henning | 233/32 X |
| 4,076,169 | 2/1978 | Schlutz | 233/14 R |

Primary Examiner—George H. Krizmanich
Attorney, Agent, or Firm—Alvin H. Fritschler

[57] ABSTRACT

A disposable, rotatable, multi-pointed, star-shaped enclosure for use in a centrifuge apparatus for the separation and washing of blood, into which fluids, such as blood containing unwanted constituents and wash agents are introduced and from which the washed blood, wash fluids and unwanted constituents are removed.

21 Claims, 8 Drawing Figures

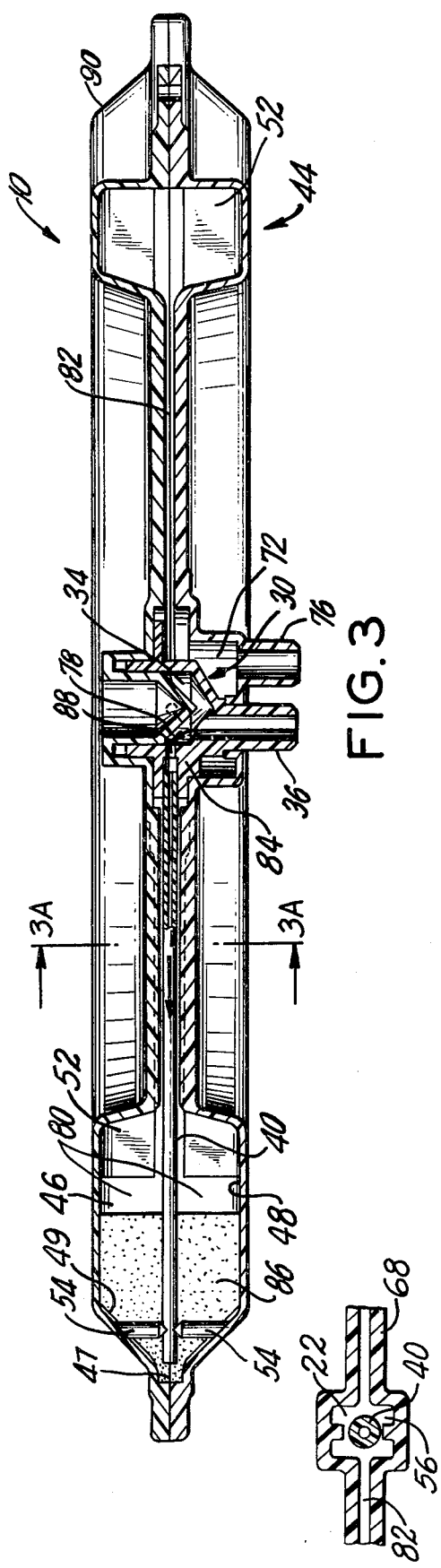
FIG. 3
FIG. 3A
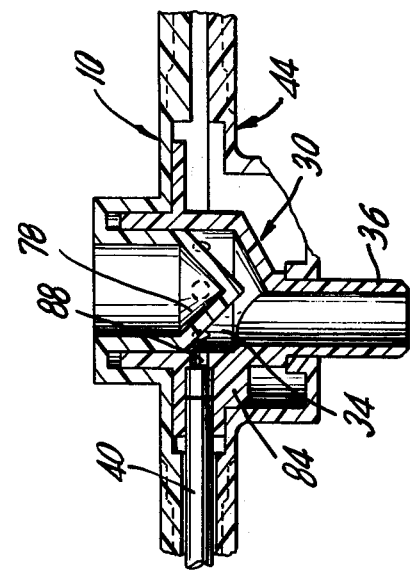
FIG. 5
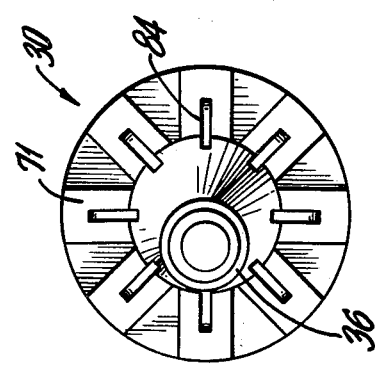
FIG. 4a
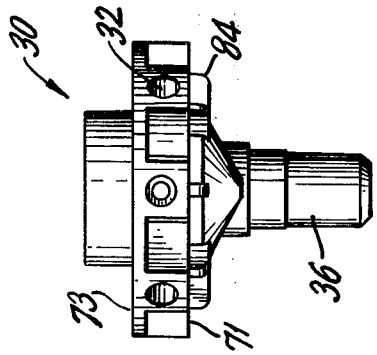
FIG. 4

DISPOSABLE, ROTATABLE, STAR-SHAPED ENCLOSURE FOR USE WITH BLOOD WASHING APPARATUS

BACKGROUND OF THE INVENTION

1. Field of the Invention

This invention relates to a centrifuge apparatus for separating and/or washing finely-divided solids suspended in a liquid, such as blood. More particularly, the present invention relates to a disposable, rotatable, multi-pointed, star-shaped enclosure for use with such an apparatus.

2. Description of the Prior Art

Blood washing is a procedure known in the art. Various devices have been proposed for washing blood to remove unwanted constituents such as contaminants, toxicants, viruses, medicants, glycerines and the like. Many of these devices center around an operation for separating the blood cells, especially the red blood cells from the plasma and, after washing the blood cells, resuspending the cells in uncontaminated plasma or other suitable blood cell resuspending liquid. This is particularly useful for blood bank purposes where contaminants such as unwanted white cells or glycerines are washed from the blood and the washed blood can then be used in the blood bank.

In another mode of use, blood containing unwanted medicants, such as barbiturates and the like, can be washed and then introduced to the donor/patient. Similarly, allergens and serum proteins can be washed from blood. Also, the devices and methods can be used to deglycerinate previously frozen but thawed whole blood (frozen blood has glycerin added thereto) or to remove cellular debris from whole blood since particles of different densities will form different layers in a centrifuge. Other similar kinds of separation and/or washing operations can be performed with these known devices.

While a wide variety of devices have been proposed in the art, the most successful devices are based upon a centrifugal separation of the blood cells from the plasma, with subsequent counter-flow washing of the blood cells. For example, whole blood is placed in a centrifuge device, which, upon revolving, forces the cells into discrete areas where the blood cells are compacted. Thereafter a washing solution, such as a sterile saline solution, is passed through the compacted blood cells to wash those cells of unwanted constituents.

Examples of these prior art centrifuge apparatuses for separating and washing blood are found in U.S. Pat. Nos. 3,347,454; 3,561,671; 3,724,747 and 3,982,691. In U.S. Pat. No. 3,982,691 and in divisional application Ser. No. 714,651, filed Aug. 16, 1976, assigned to the same assignee as this application, there is described an apparatus which included a rotatable enclosure having an injector for moving suspended blood cells as well as liquids into and out of the enclosure; a plurality of angularly shaped blood cell receiving areas in fluid communication with each other and evenly spaced about the longitudinal periphery of the enclosure and forming a part of the enclosure, wherein at least one pair of opposite wall portions of each receiving area converge toward the periphery of the enclosure forming a locus of maximum centrifugal force in the rotating enclosure at the apexes formed by the juncture of the converging wall portions; and a plurality of independent conduits in fluid communication with each other, each with one end thereof in fluid communication with the injector and the other end thereof connected to the locus of maximum centrifugal force.

OBJECTS OF THE INVENTION

The rotating enclosure in U.S. Pat. No. 3,982,691 and divisional application Ser. No. 714,651, has made for a significant advance in the art. The present invention is considered to be an improvement on the invention of divisional application Ser. No. 714,651 and its main features and objectives are thus similar to those of the aforesaid divisional application.

Experience gained in developing the invention of divisional application Ser. No. 714,651 has indicated the desirability of some improvements in apparatus and has led to the conception and development of the present invention which has, in addition to the advantages and features of the earlier invention, greatly enhanced ability to completely wash blood cells in a contamination-free, rapid and efficient manner.

A further advantage of the invention is the provision of an improved disposable, rotatable, multi-pointed, star-shaped enclosure that lends itself to volume production and increased efficiency in blood cell washing and recovery of blood cells after washing. This invention further provides a simplified system of fluid distribution into and out of the rotating enclosure, particularly suitable for use in conjunction with a counter rotating tube unwinding device as discussed subsequently herein. Another advantage provided by the present invention is a centrifuge rotor to contain the semiflexible, disposable, rotating, multi-pointed, star-shaped enclosure against the pressure created by the centrifugal forces.

These and other objects of the invention will be the more readily appreciated and understood from the ensuing disclosure and claims.

BRIEF DESCRIPTION OF THE INVENTION

Briefly, the present invention provides a disposable, rotatable, multi-pointed, star-shaped enclosure for use in a centrifuge apparatus wherein finely-divided solid particulate material, especially biological particulate material such as blood cells, may be separated and/or washed. The centrifuge apparatus provides means for rotating the rotatable enclosure and thus centrifuging solid particulate material contained therein, whereby the particulate material is collected in discrete areas of the enclosure in the form of a dense suspension under the centrifugal force exerted in the centrifuge. This separation of the particulate material also allows a washing step to be performed in discrete compartments of the enclosure. A liquid, less dense than the particulate material, may be passed through the dense suspension of particulate material from the outer-most periphery of each such compartment toward the axis of rotation of the centrifuge. An important feature of the present invention is that all of the parts of the particulate material are subjected to the flow of the liquid therethrough. This is especially useful in washing contaminants from blood, e.g., whole blood, and the invention will be illustrated with that embodiment.

The centrifuge apparatus for separating and washing blood employs an enclosure means for enclosing and biologically isolating a quantity of blood cells in a suspending liquid, e.g., plasma or other suspending liquid. A rotation means is provided for rotating the enclosure means about its vertical axis. This establishes a centrifugal force in the transverse (horizontal) direction of the enclosure means, which force is greatest at the periphery of the enclosure means. A fluid distribution means is provided for moving liquid-suspended blood cells and wash reagents into and out of the enclosure means and a drainage means is provided for moving contaminated wash agents out of the enclosure means. The fluid distribution means and the drainage means move these fluids in and out of the enclosure means, respectively, in a manner which keeps the system biologically isolated, e.g., sterile. Moreover, the fluid distribution means and drainage means are an integral part of the enclosure means and substantially contained therewithin. The need for a rotating seal has been eliminated by use of a counterrotating tube unwinding device. Accordingly, a continuous washing system can thereby be provided.

As a very important feature of the invention, there is provided a plurality of symmetrically shaped blood cell receiving compartments which are evenly spaced about the periphery of the enclosure means and symmetrical with respect to a plurality of imaginary radial lines extending from the vertical axis of the enclosure means through the center of each of the compartments and lying in a plane normal to the vertical axis of the enclosure means. Any number of such receiving compartments may be used, e.g., 2 to 100 or more, especially 4 to 12, and particularly 6 to 8, so long as the receiving compartments have approximately equal radians or parts thereof between each adjacent receiving compartment in order to provide acceptable balance in the rotating centrifuge. These symmetrically shaped blood cell receiving compartments form at least a part of the outer periphery of the enclosure means. To provide the symmetrically shaped, compartments, there must be at least two opposed side wall portions of the blood cell receiving means symmetrical about one of the radial lines referred to hereinabove and at least two upper and lower opposed wall portions symmetrical not only about one of the radial lines but also about the plane normal to the longitudinal axis referred to hereinabove. The upper, lower and side wall portions converge toward one of the radial lines at the longitudinal periphery of the enclosure means. Particularly preferred is an embodiment having 2 pairs of triangularly shaped, opposed side, upper and lower wall portions which converge at the periphery of the enclosure means to form a pyramid-like shape whose outermost point (the vertex) coincides with the locus of maximum centrifugal force.

A locus of maximum centrifugal force in the rotating enclosure means is established at or about the apexes formed by juncture of the converging wall portions. Thus, the blood cells will be separated from at least some of the plasma and, thus, at least form a dense suspension in this symmetrically shaped receiving compartment and the maximum density of the suspension will be at the locus of maximum centrifugal force. The angles of convergence can affect the efficiency of separation of blood cells from plasma and, thus, the density of the suspension of the blood cells. Angles between 20° and 135°, especially between 35° and 115° are preferred. Usually, angles 90° or less will be used. Within these ranges of angles (along with the angular speed of rotation) the density of the suspension may vary considerably. In any case, however, the blood cells are compacted (i.e., contained in a small volume) and for the sake of simplicity the compaction will be hereinafter referenced.

Each of the symmetrical receiving compartments is further defined by upper and lower annular wall portions within the enclosure means spaced apart from one another to define an port to an inner passage within the enclosure means in fluid communication with both the compartment and the center of the enclosure. This inner passage is defined by upper and lower plateaus extending interiorly of the receiving compartments and facing one another. The plateaus are spaced apart to provide the inner passage and the periphery walls of the upper and lower plateaus correspond to the upper and lower annular wall portions, respectively. The upper and lower annular wall portions are concentric with the center of the enclosure means base and intersect the upper and lower opposed wall portions previously described, respectively. This intersection helps define a predetermined volume for each compartment as discussed subsequently. The upper and lower wall portions are also symmetrical with respect to the plane referred to previously which is normal to the vertical axis of the enclosure means.

Each of the upper and lower annular wall portions is inclined toward the vertical axis of the enclosure means thereby forming conical sections which resemble the groove in a V-shaped pulley.

Each symmetrically shaped receiving compartment of the present invention is a prismatic compartment having a predetermined volume. This predetermined volume is at least twice the initial volume of blood cells to be washed in the enclosure means divided by the number of receiving compartments employed. For example, blood is normally received from a donor in a standard unit of 500 ml. This unit, except for isolated purposes, is normally handled as a separate unit and not mixed with other blood. This allows the pedigree and history of the blood to be known. To handle 500 ml. of blood containing up to 300 ml. of blood cells in an enclosure means having eight receiving means, each predetermined volume would be at least 75 ml.

In a preferred embodiment, the shape of the prismatic compartment is pentaprismatic with a curved base and substantially rectangular lateral faces. Two opposed converging side wall portions defining an apex of the receiving compartment also define the pinnacle of the pentaprismatic compartment. The base of the pentaprismatic compartment is defined by the annular wall portions within the enclosure means previously discussed herein. The remaining two side wall portions of the pentaprismatic compartment are defined by radial walls within the enclosure means and intersecting both the annular wall portions (the base) and the two converging side walls portions defining the pinnacle of the pentaprismatic compartment at the line defined by the intersection of two adjacent converging side wall portions of two adjacent receiving compartments. The upper and lower surfaces of the pentaprismatic compartment are defined by the upper and lower planar surfaces of the enclosure means which are substantially normal to the vertical axis thereof.

The pinnacle portion of the pentaprismatic compartment is further defined as a pyramid-like structure whose vertex coincides with the pinnacle and whose (imaginary) base defines the frustum of the pentaprismatic compartment.

The diameter of the annular wall portion should be sufficient to afford the predetermined volume in each receiving compartment in conjunction with the other wall portions defining the prismatic compartment.

Another important feature of the invention is a plurality of independent conduit means each of which has one end connected to the fluid distribution means and the other end terminating in the vicinity of the locus of maximum centrifugal force in one of the symmetrically shaped blood cell receiving compartments. Thus, there are provided independent and separate fluid passageways from the fluid distribution means to the locus of maximum centrifugal force. The independent conduit means are located completely within the enclosure means and extend radially outward from the fluid distribution means through the axis of symmetry of each receiving compartment. This insures the uniform and symmetrical dispersion of fluids flowing through the independent conduit means, from the independent conduit means, at a radius of equal centrifugal force developed within the rotating enclosure means.

Each independent conduit means terminates substantially at or in the proximate vicinity of the (apex) locus of maximum centrifugal force of a receiving compartment, allowing for fluid flow from the conduit means through the volume surrounding the conduit. It has been found that the stream of wash fluid flowing from the independent conduit means in this arrangement reaches the locus before reversing direction and creates a wavefront along the curved plane of equal centrifugal force towards the center of the enclosure means.

The arrangement of the present invention insures complete washing of the packed blood cells within a receiving compartment, as opposed to an asymmetrical arrangement wherein the independent conduit means are located outside the receiving compartment and do not pass through the symmetrical center thereof, the receiving compartment itself is asymmetrical in shape, and the fluids are introduced directly at the locus of maximum centrifugal force through the bottom wall of the receiving compartment in a substantially vertically upwards direction.

In this type of asymmetrical arrangement, there is the potential for unequal distribution of the wash fluid through the packed blood cells. This problem cannot be solved by simply increasing the pressure used to feed the wash fluid. If the pressure used to feed the wash fluid were increased so as to improve its distribution throughout the packed blood cells, another problem would be created, i.e., removal of the cells along with the wash fluid. In the symmetrical arrangement of the present invention, however, there is equal distribution of the fluids because the fluid must completely reverse its direction of flow at the locus and spread uniformly back along the longitudinal axis of the conduit means.

Another feature of the present invention is the fluid distribution means concentrically located within the enclosure means which comprises a wheel-like disposable member. The wheel-like member comprises a single molded part, preferably plastic, with a single inlet port for receiving fluids introduced into the enclosure means and a plurality of outlet ports such as radial sockets for affixing an equal number of, independent conduit means which extend radially outwardly toward the apexes of the receiving compartments. These independent conduits may be secured within the sockets by cementing with a suitable solvent, e.g., ethylene dichloride for polycarbonate materials or by mechanical means such as press fits.

The fluid distribution means conducts fluids through the single inlet port, preferably located at its bottom, into a concentrically located manifold chamber therein and in fluid communication with the inlet port and the outlet ports. A conically shaped plug extends into the manifold chamber from the top portion of the enclosure means defining a radially outwardly directed fluid path within the manifold chamber between the inlet port and the independent conduits. This prevents the development of turbulence and air pockets within the manifold chamber during priming and the danger of air bubbles blocking the independent conduit means.

The sum of the cross-sectional areas of the independent conduit means must be less than the cross-sectional area of the inlet conduit in order to create an amount of back pressure in the manifold chamber sufficient to assure equal flow and discharge of fluids from the independent conduits. This in turn assures symmetrical loading of each receiving compartment.

The drainage means is concentrically located within the enclosure means and comprises a sump member having an outlet port in fluid communication with the inner annular cavity previously described. The drainage means removes contaminated wash fluids from the symmetrical receiving compartments out of the enclosure means.

Power means for rotating the rotation means and enclosure means are provided. The speed of angular rotation should be sufficient to separate the blood cells from the suspending liquid and compact the blood cells in the blood cell receiving compartments.

Control means are provided for controlling liquid flows through the fluid distribution means, drainage means, conduit means, blood cell receiving compartments and enclosure means. The control means allow for the flowing of suspended blood cells into each of the blood cell receiving compartments, for the flowing of a wash agent through each of the said conduit means and then through the compacted blood cells in each of the blood cell receiving compartments, and for the flowing of resuspended blood cells from each of the receiving compartments through each, respective, conduit means, through the drainage means and out of the centrifuge apparatus.

The power means and control means are conventional apparatus in the art and function in their conventional manners.

With the foregoing arrangement, the basic operation of the method and apparatus is as follows. Red blood cells in a suspending liquid, such as plasma or artificial plasma, are flowed through the fluid distribution means, then through the conduit means and into the blood cell receiving compartments of the enclosure means. Since each of the symmetrically shaped blood cell receiving compartments is independently connected to the fluid distribution means by the plurality of respective independent conduit means, a plurality of receiving compartments can be simultaneously filled with suspended blood cells. Thus, the centrifuge apparatus can be loaded with the blood while the centrifuge is rotating.

The distribution means assures equal amounts of blood will be delivered to each receiving compartments due to the back pressure in the manifold chamber which assures equal flow in each independent conduit means. The rotation of the enclosure means forces the blood cells towards the apexes of the receiving compartments and maintains the blood cells in such locations. After sufficient centrifugal force is generated on the suspended blood cells, the heavier solid particulate blood cells will be forced toward the locus of maximum centrifugal force and compacted in that region. The suspending liquid, on the other hand, will be displaced from the locus of maximum centrifugal force toward the axis of rotation of the enclosure means. After that separation has been accomplished by sufficient centrifugal force, then the blood cells can be washed by flowing a wash agent through each of the independent conduit means and then through the blood cells in each of the blood cell receiving compartments. After washing has taken place, the wash agent is displaced from the locus of maximum centrifugal force towards the axis of rotation of the enclosure means. Thereafter, the blood cells are resuspended in a liquid and removed from the apparatus through the independent conduit means and distribution means. Of course, as described above, the drainage means is at the axis of rotation and moves the contaminated wash solutions from the enclosure means to the outside of the centrifuge apparatus.

As another important feature of the invention, after the washing has taken place as described above, the washed blood cells can be removed from the blood cell receiving means through each of the respective conduit means and subsequently through the fluid distribution means and out of the centrifuge apparatus, while the centrifuge apparatus is being rotated. This may be accomplished, among other ways, simply by flowing a wash agent through the drainage means and through the inner passage within the enclosure means into each of the receiving compartments, thereby forcing the compacted and washed blood cells from the receiving compartments, through the conduit means and out of the centrifuge apparatus via the fluid distribution means. Of course, when the blood cells are so "unloaded", the rotational speed of the centrifuge is considerably reduced, e.g., for a 12-inch enclosure below 400 RPM. This counter flow of fluid is accomplished simply by placing a pressure head on the counter flowing fluid greater than the pressure developed by the lower rotational speed of the centrifuge during that "unloading" step. A pressure differential exerted by the resuspending liquid across the compacted blood cells of at least about $\frac{1}{4}$ pound will normally be used.

From the foregoing, it can be seen that the centrifuge can be continuously operated in that blood cells, suspended in natural plasma or artificial plasma, can be "loaded" into the centrifuge, separated by centrifugal force, washed, and "unloaded" from the centrifuge without the centrifuge ever being completely stopped. Only the difference in rotational speeds are required for the steps. This is possible since the washing step fully cleanses the fluid distribution means, conduit means and blood cell receiving compartments prior to the "unloading" step, so that the cleaned blood cells flow only through this previously cleaned fluid path.

It should be further appreciated that since the washing agent enters the receiving compartments, from the conduit means, substantially at the point of maximum centrifugal force, the washing agent passes symmetrically through essentially all of the compacted blood cells.

The present arrangement operates without the use of rotating seals, which are expensive to manufacture and add the possibility of contamination of the blood being processed. A counter rotating device employing a speed ratio of 2 to 1 as illustrated in U.S. Pat. Nos. 3,586,413 and 3,986,442 the disclosures therein relating to the operation of the counter rotating device incorporated herein by reference is employed in conjunction with the centrifuge apparatus to prevent the inlet and outlet conduits from becoming twisted during rotation of the enclosure means about its longitudinal axis.

Also, by reason of the present arrangement, as discussed above, a disposable enclosure means with the blood cell receiving compartments can be provided and that arrangement allows for rapid removal of the disposable enclosure means. Thus, the enclosure means may be constructed of any inert material which can be releasably held by the rotation means of the centrifuge. In this regard, the rotation means will have at least one cavity therein for receiving and retaining enclosure means during rotation thereof. This will, of course, require that the cavity of the rotation means and the enclosure means have complementary shapes so that the enclosure means may be periodically removed from the cavity of the rotation means and replaced by a new enclosure means. Of course, with such an arrangement, it is most convenient that the enclosure means, the conduit means and the fluid distribution means form a replaceable and disposable unitary structure. In view of the intended disposable nature thereof the so produced unitary structure is preferably made, principally, of a moldable material, and especially an extendable material so that small differences in the complementary shapes of the disposable receiving compartments and the cavity in the rotating means can be compensated for by extension of the enclosure means. In other words, the shape of the unitary structure can therefore be conformed to the shape of the cavity in the rotation means by action of centrifugal forces on the unitary structure during the rotation thereof.

Other important features of the invention and advantages of the invention over the prior art will be apparent from the following detailed description of the invention.

BRIEF DESCRIPTION OF THE DRAWINGS

FIG. 3 is a side elevation view partly in cross-section of the enclosure means taken through line 3—3 of FIG. 2.

FIG. 4 is a side elevation view of a wheel-like distribution member shown in the enclosure means of FIG. 1.

FIG. 4a is a bottom view of the wheel-like distribution member shown in the enclosure means of FIG. 1.

FIG. 5 is an enlarged cross-sectional view of the wheel-like distribution member shown sandwiched between the upper and lower halves of the disposable enclosure means.

DETAILED DESCRIPTION OF THE INVENTION

Figure 1:
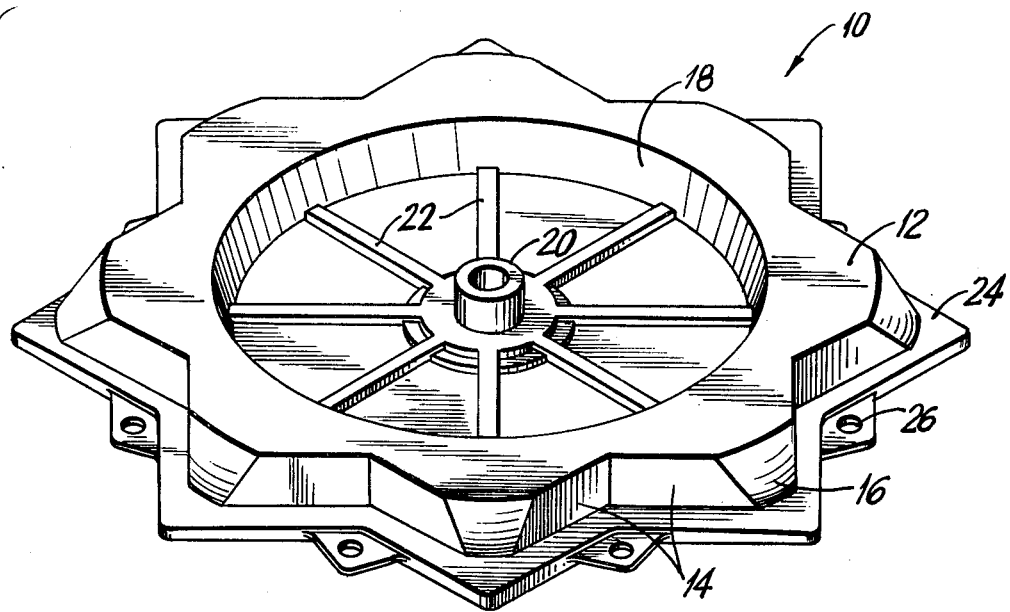
FIG. 1 is a perspective exploded view showing a disposable enclosure means embodiment of the present invention.
Figure 1:
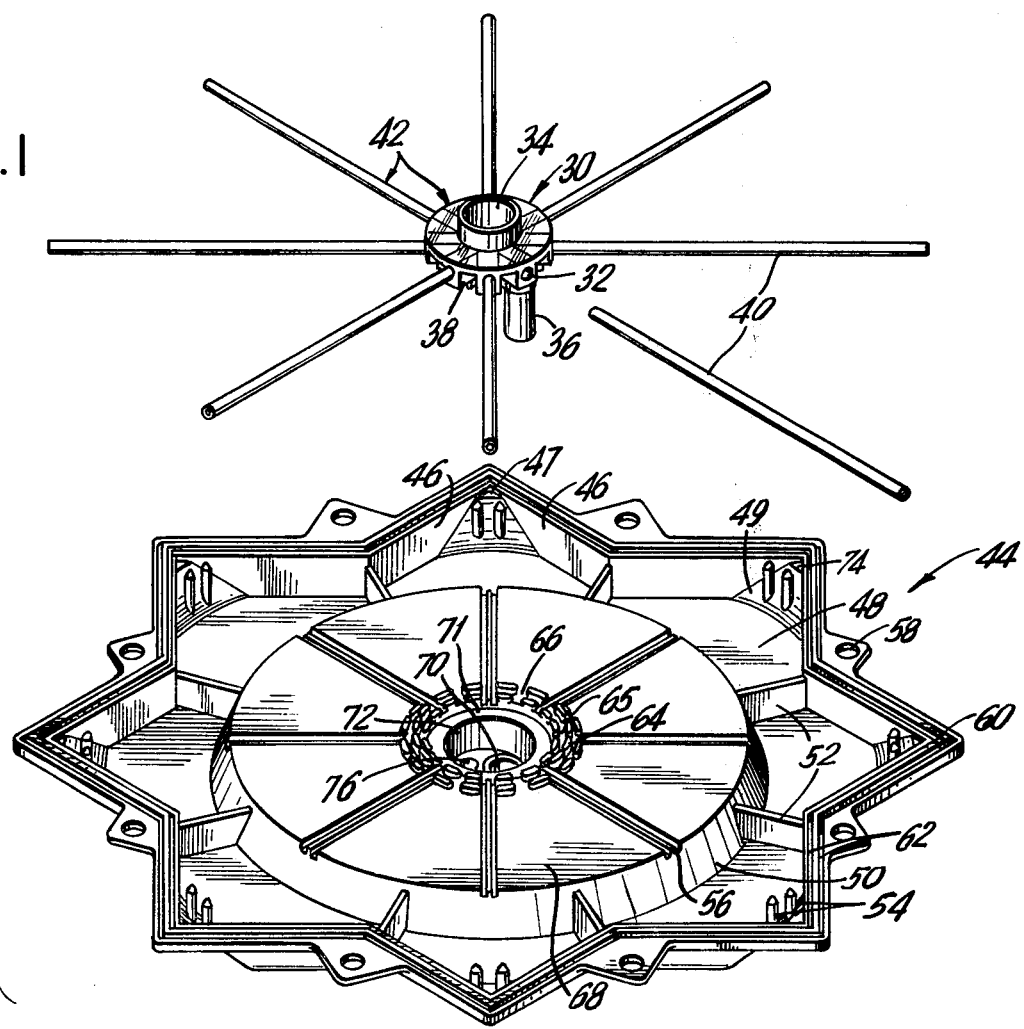

The invention can best be understood by specific reference to FIG. 1 where the principles of the invention are illustrated in terms of a specific assembly. The assembly of that embodiment is composed of four main assembly components: upper half 10 of the enclosure means, wheel-like member 30, conduits 40, and lower half 44 of the enclosure means. The upper half 10 of the disposable, rotatable enclosure means of this invention is shown as an octagonally shaped plastic molding configured to provide the top of surface 12 of eight receiving compartments. Also shown are the upper surface 14 of the side walls of the receiving compartments, the top surface 16 of the and the apex portion of the enclosure means. The upper half of annular wall 18 which defines the base portion of pentaprismatic-shaped receiving compartments.

At the center of the upper half 10 of the disposable enclosure means, there is a boss 20 which supports a tapered plug which in turn seals the manifold cavity 34 of the wheel-like member 30.

Eight sockets 32 of the wheel-like member 30 comprising the fluid distribution means receive eight independent conduits 40. The independent conduits 40 are pressed or solvent cemented into sockets 32 of the wheel-like member 30. As shown in FIG. 1, the eight independent conduits lie in a plane normal to the vertical axis of the enclosure means and are equally spaced apart thus constituting the "spokes" of the wheel. Between sockets 32 are an equal number of ports 38 which allow fluid communication between the inner passage of the enclosure means the the exit port 76 of sump 72.

Inlet port nipple 36 located at the lower portion of wheel-like member 30 press fits into hole 70 situated in sump 72 in the lower half 44 of the enclosure means. The inlet port nipple 36 provides a means for attaching tubing thereto for flow of wash fluids and blood into the fluid distribution means, for distribution to each radial conduit 40, and for flow of washed red cell suspension, from the receiving compartments out of the enclosure means.

Referring to the lower half 44 of the disposable rotatable enclosure means of this invention, there is shown a substantially symmetrical half with all the compartments exposed. Each lower half of a blood cell receiving compartment is comprised of six surfaces. Opposed side walls 46 converge toward apex 47 at the periphery of the enclosure means. The lower half of radial partial side walls 52 connects the inner convergence of adjacent side walls 46 with the lower half of partial annular wall 50. Lower wall 49 of the pyramidal apex portion of the enclosure means is complementary to upper surface 16. Lower surface 48 of the eight receiving compartments complements upper surface 12.

Conduit support studs 54 are situated on surface 49, close to the apex of each receiving compartment. Studs 54 are vertically oriented and spaced apart a distance sufficient to capture the end of each radial independent conduit 40 terminating in the proximate vicinity of the apex of each receiving compartment. The purpose of studs 54 is to secure the location of the free end (the one end not connected to socket 32) of conduit 40, i.e., locate the conduit centrally substantially at the apex 47 and prevent its vibration, which could agitate the blood cells and cause channeling of wash fluids. Moreover, the ends of studs 54 extending into the receiving compartments are preferably chamfered about 45° (FIG. 3). When abutted and aligned stud point to stud point during assembly of the upper and lower halves of the enclosure means, a surface of each stud becomes tangent to the circumference of an independent conduit and prevents the displacement of the conduit toward that stud. The four stud surfaces tangent to the circumference of an independent conduit define a substantially rectangularly shaped enclosure for restricting movement of the conduit captured therebetween in both coordinate directions, i.e., up and down and side to side. The space between studs 54 is also sufficient to permit return flow of fluids between and around the conduit means.

In addition to being supported by studs 54, each independent conduit 40 is supported by channels within upper (not shown) and lower plateau 68. Upper channel half 22 in conjunction with lower channel half 56 define a channel which supports conduit 40 therein.

Alignment holes 26 and 58 are located at the perimeter of the upper and lower halves and are in registry during welding thereof. Referring to the lower half 44 of the enclosure means there is exposed to view raised welding land 60 around the perimeter of the enclosure means. A corresponding welding land (not shown) exists around the perimeter of the upper half 10 of the enclosure means. During hot plate welding, this land 60 is melted and, when fused with corresponding meltable land on the upper half 10, completes the sealing of the two halves in the disposable enclosure means of this invention. Surplus melted material from the melted lands flows sideways into troughs 62 in lower half 44 and corresponding troughs (not shown) in upper half 10, the troughs also situated along the perimeters of the upper and lower halves 10 and 44 and adjacent to the meltable lands.

A second welding area exists concentric with and circumferential about the sump 72 in the lower half 44 and a mating location in the upper half 10. Hot plate welding of the corresponding lands 64 and troughs 65 (lower half 44) of the enclosure means occurs as described hereinabove. However, inner welding lands 64 are segmented by radial passageways 66 therebetween to the leading inner passage 82 within the enclosure means. The weld points are staggered to form radial passageways 66 between the welded lands so as to allow return flow of wash fluids into the sump 72.

Referring to FIGS. 1, 2, 3 and 6 the enclosure means assembly can be understood by following the subsequently described typical assembly sequence. Conduits 40 are pressed or solvent cemented into sockets 32 of the wheel-like member 30 which is then attached to the lower half 44 of the enclosure means by pressing inlet port nipple 36 into hole 70 in the bottom of sump 72 while aligning conduits 40 in their respective lower radial half channels 56. The upper and lower halves 10 and 44 of the enclosure means are placed in their respective welding fixtures with the upper half 10 locating on dowel pins or the like which protrude through registration alignment holes 26 and 58.

The two halves 10 and 44 are pressed against a hot plate suspended between them. Then welding lands 60 become soft. The hot plate is then withdrawn and the two halves are pressed together; the tapered plug centrally located in the upper half 10 of the enclosure means is pressed into cavity 34 at the top of wheel-like member 30 thereby sealing cavity 34. Excess plastic softened in lands 60 and 64 flow into their associated troughs 62 and 65, respectively as the two halves of the enclosure means are thereby fused together to form an integral assembly.

Referring to FIGS. 3, 4, 4a and 5, the wheel-like member 30 has centering lugs 84 located concentrically on the underside thereof. When the wheel-like member 30 is piloted into sump 72, the inlet nipple 36 is pressed into hole 70 of sump 72 and extends therethrough. The center lugs 84 fit within the annular walls of sump 72. The underside of sockets 32 of wheel-like member 30 rest on an annular ledge 71 within sump 72, thereby positioning the radial independent conduits 40 in a plane normal to the vertical axis of the enclosure means and in channels 56 of plateau 68. When conical plug 78 is inserted into the manifold chamber 34, its penetration thereinto is controlled by the abutting of upper ledge 73 of the wheel-like member with the hub portion of upper enclosure molding 10. The plug 78 penetration into manifold chamber 34 seals the chamber and prevents displacement of the fluid distribution means in a vertical direction. Moreover, the conically shaped plug 78 aids in guiding flow of fluids through the manifold chamber 34 between the inlet nipple 36 and exit ports 88. Inlet nipple 36 and exit ports 88 will be hereinafter referred to as such, regardless of the fact that the direction of liquid flow through the manifold chamber may be and is reversed during operation.

Referring to FIGS. 3, 3a, and 5, upper and lower plateaus are spaced apart thus defining inner passage 82. Passage 82 is traversed by conduit 40 along plateau half-channels 56 and 22 and it is in fluid communication with both the receiving compartments 80, through the port formed at the outer periphery of the plateaus by the spacing between upper and lower annular walls 18 and 50, and with sump 72 at the radially inner end of the plateaus via radial passageways 64 and channels 56 and 22.

Passage 82 allows wash solution overflow to enter sump 72 from the compartments without turbulent flow of wash fluid, i.e. without back pressure. For this purpose, the total cross-sectional area of passageways 66 and channels 56 and 22 should be greater than or equal to the cross sectional area of outlet nipple 76 of sump 72.

It is preferred, however, that the integral and unitary structure be interlocked by at least a heat seal between the interlocking elements, as described above. Of course, the particular method and arrangement of assembling the unitary structure of the disposable enclosure is not at all critical and may be practiced as desired. The foregoing simply illustrated a suitable method for manufacturing of the unitary structure.

Figure 2:
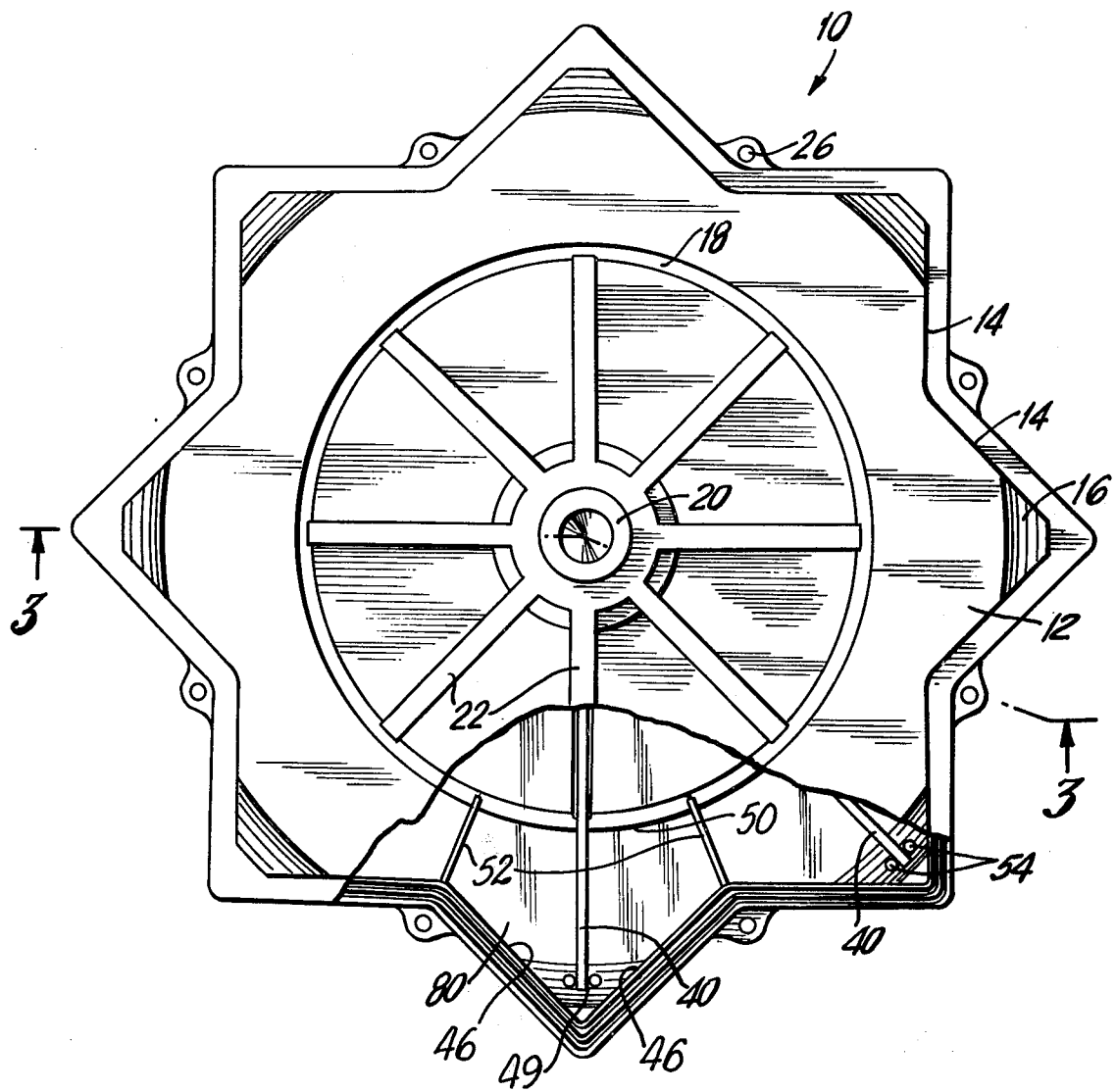
FIG. 2 is a plan view of the disposable enclosure means partly in cross-section.
Figure 6:
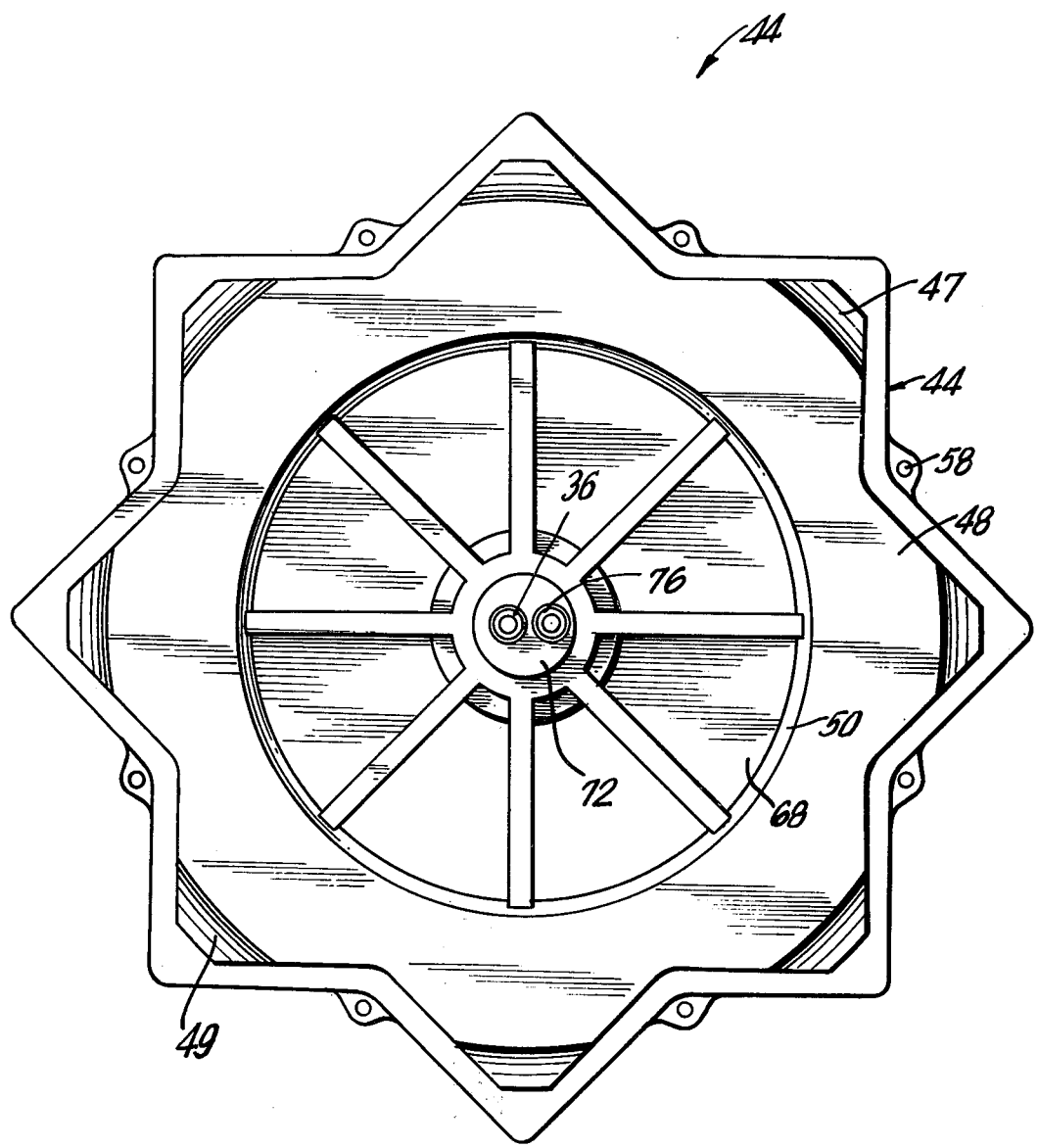
FIG. 6 is a bottom view of the disposable enclosure means with the wheel-like distribution member in place.

When the assembly is in rotation, at operational rpms, sufficient centrifugal force develops so that the solid particulate matter in the enclosure means collects in the pyramid-like portions of the receiving compartments, generally 80, bounded by wall portions 46, 49, 48, 50 and 52, FIGS. 1, 2 and 3. In this case, the blood cells are shown compacted in the receiving compartments 80 of the broken away portion shown in FIG. 3.

The compacted blood cells displace the plasma associated therewith towards the passage 82 within the enclosure means. When the separation of the blood cells has been sufficiently accomplished, a wash fluid can be introduced into inlet port 36 of the fluid distribution means and passed through manifold chamber 34, exit ports 88 and conduits 40 as shown by the arrows. The wash fluid then is uniformly and symmetrically dispersed through conduits 40 substantially at the locus of maximum centrifugal force and spreads out to wash the blood cells 86 compacted in receiving compartments 80. The wash fluid, thereafter, by virtue of a higher pressure head, passes through passage 82 through sump 72 and out of the apparatus via outlet nipple 76.

It will be appreciated that the blood cells 86 are of greater density than either the plasma normally associated therewith or the wash fluid which is subsequently used for washing the separated blood cells. Under the circumstances, the centrifugal force acting upon the blood cells will be greater than the centrifugal force acting upon either the plasma or wash fluid. Therefore, both the plasma and wash fluid can be passed through the compacted blood cells, by means of an increased pressure head above the centrifugal force on the blood cells, since the more dense blood cells will cause displacement of the plasma or the wash fluid toward sump 72 on the axis of rotation of the enclosure means, when the assembly is at operational rotational speeds.

As it can also be appreciated from the assembly of FIG. 3 and the explanation thereof, the wash fluid is introduced substantially at the apex formed at the juncture of the oppositely disposed converging wall portions of the blood cell receiving compartments. With this arrangement, the wash fluid will contact substantially all of the compacted blood cells.

With particular reference to FIG. 2, which is a top view of the disposable enclosure means, the blood cell receiving compartments, generally 80, have oppositely disposed converging wall portions 14, in a manner similar to that of FIG. 1. However, additionally, the top and bottom wall portions 16 and 49 (see FIGS. 2 and 6) also form an angle, i.e., converge. Thus, there are four opposite wall portions which converge toward a locus of maximum centrifugal force and this effects a multiplication of the efficiency of the centrifugal force exerted on the blood cells within the blood cell receiving compartments 80. This, of course, is a very advantageous feature of the present invention.

Figure 7:
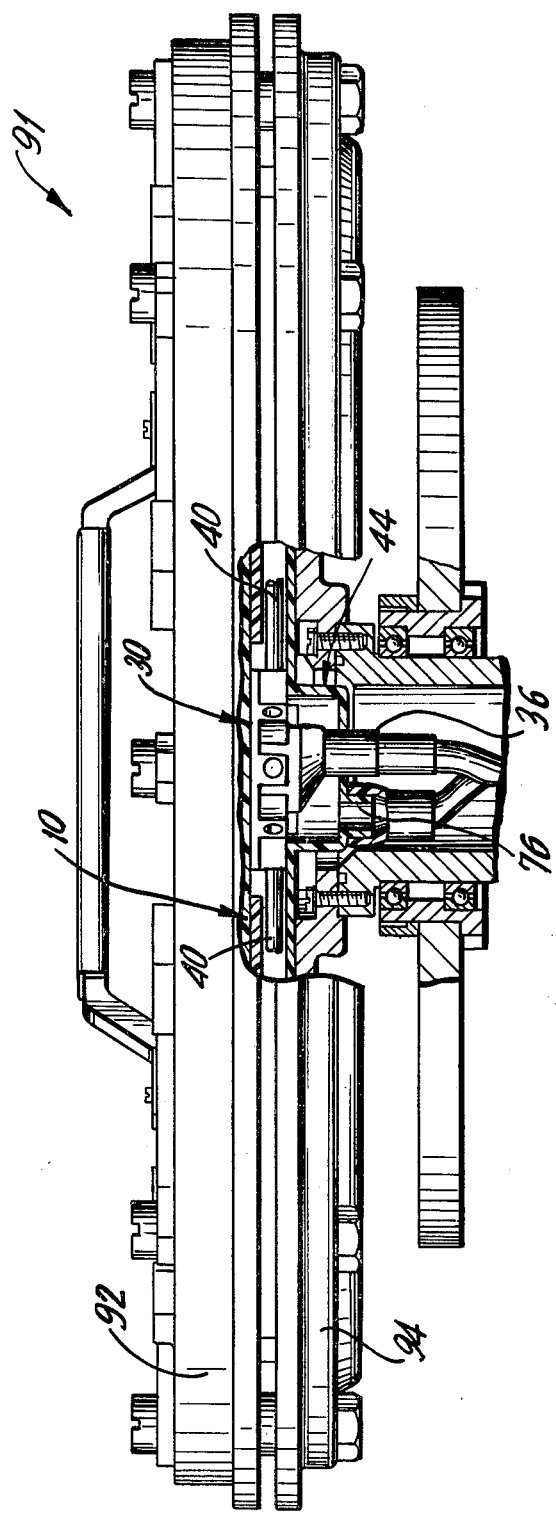
FIG. 7 is a side view of the enclosure means mounted in a centrifuge rotor.

Referring to FIG. 7, wherein the disposable enclosure means is shown in place in the rotor 91, the disposable enclosure means 90 is replaceable within the cavity formed by lower support plate 94 and upper support plate 92, simply by separating upper support plate 92 from lower support plate 94. The disposable enclosure 90 is then removed from lower support plate 94 and can be discarded. The disposable enclosure is a unitary structure consisting of the blood cell receiving compartments 80, the fluid distribution means 30, the drainage means 72 and the conduit means 40. Since the entire enclosure is disposable, no cleaning of the centrifuge is required. While not shown in the drawings, the centrifuge apparatus will also have associated therewith reservoirs, pumps and receiving containers for flowing blood, wash liquid and the like into and receiving washed blood out of the apparatus. Of course, the apparatus will also have associated therewith a power means and driving mechanism, such as motors, speed controllers and the like, for rotating the rotation means and enclosure means with sufficient angular rotation to separate the blood cells from the suspending liquid (plasma) and compact the blood cells in the receiving compartments. Also provided are control means controlling the rotation of the centrifuge and the flow of the various liquids, as described above. These associated devices, power sources and controllers are known to the art and need not be described herein. In this regard, reference is made particularly to the U.S. patents and publications mentioned hereinbefore.

In operation, the apparatus is provided with reservoirs of blood and washing fluid which can be sequentially directed into inlet nipple 36, by appropriate and conventional flow control means (not shown). A pump, biologically acceptable, forces blood from the reservoir into inlet nipple 36, through manifold chamber 34 and of exit ports 88, through conduits 40, into the receiving compartments 80. In this regard, the enclosure, as defined above, has a plurality of symmetrically shaped blood cell receiving compartments. These compartments are evenly spaced, as defined hereinbefore, about the periphery of the enclosure. Also as discussed above, at least four opposite wall portions of each of the compartments converge toward the periphery of the enclosure. Likewise, as discussed above, the conduits have one end in communication with the blood supply and the other end in communication with the apexes of the converging wall portions of each of the blood cell receiving compartments.

The enclosure, held in the cavity of the centrifuge, is rotated first at a lower angular speed about its vertical transverse axis to effect even distribution of the blood within the enclosure. This can be practiced simply by bringing the centrifuge up to operational rotational speeds for separating the blood cells, as discussed below. After the rotation of the enclosure has commenced, the speed of angular rotation is increased until there is sufficient centrifugal force exerted on the blood whereby the blood cells, especially the red blood cells, are separated from the liquid portion of the blood (the plasma) and the red blood cells are compacted and relatively evenly distributed in the receiving compartments Once this separation of blood cells has been accomplished, a wash fluid is then flowed from a convenient wash fluid supply source, which is in communication with one end of the conduit as previously described, through the conduits 40, into the apexes of the converging wall portions of the compartments 80, through the compacted blood cells and through passage 82 of the enclosure. Of course, the wash liquid finally exits from the centrifuge through outlet port 76 of sump 72. This flow of wash liquid is continued until the red blood cells are washed substantially free of contaminants, as discussed above. It should also be noted that the washing liquid will similarly wash the enclosure, sump 72 and outlet nipple 76 at that same time.

Thereafter, the angular speed of rotation of the enclosure is reduced so that the compacted blood cells in the receiving compartments may be resuspended during deceleration vibration of the centrifuge. Resuspending liquid is then flowed into the enclosure via outlet nipple 76, through annular cavity 82 and into compartments 80. The flow of the resuspended blood cells continues from the compartments 80 through the conduits 40 and into a suitable collecting reservoir via manifold chamber 34 and inlet nipple 36.

Thus, it will be appreciated that the washed blood cells are passed countercurrently back through the apparatus and in the pathway which has been fully washed by the wash fluid in washing the red blood cells. This avoids any chance of contamination of the washed blood and is an important feature of the invention. Additionally, it should be fully understood that the washing with the wash fluid commences as the wash fluid enters the compartment through conduit 40. This conduit end is substantially at the point of maximum centrifugal force and will therefore contact all parts of the compacted blood cells.

The particular angular speeds of rotation can vary considerably depending upon the specific diameters of the enclosure and compartments. Obviously, for larger diameter enclosures, sufficient centrifugal force will be developed at much lower angular speeds than will be required for smaller diameter enclosures. However, as an indication of appropriate speeds, sufficient centrifugal force will be developed in a 12-inch diameter enclosure when the angular speed or between 1500 and 5000 revolutions per minute, more often between 2000 and 4000 revolutions per minute, e.g., around 3000 revolutions per minute. The temperature at which the process is carried out is not critical and may be carried out at any temperature above the freezing point or coagulation point of the blood and below the denaturing point of the blood. Generally, temperatures between about 40° F. and 120° F. are satisfactory, especially between about 60° F. and 90° F. The process is operated under pressures generated by the centrifugal force and in combination with the head pressure exerted by the wash fluid during the washing step. In these latter regards, it is only necessary to supply the wash fluid at head pressures great enough to flow the wash fluid or the resuspended blood cells against the centrifugal force for passing the wash fluid or resuspended blood cells out of the centrifuge. An adjustable pump in this regard is desirable so that the pressure for causing such flows can be readily obtained with different rpms of operation.

Other modifications and alternatives of the present apparatus and process will be further apparent to those skilled in the art, beyond those mentioned above. Thus, the present specification and claim language are intended to embrace those above-noted and further alternate embodiments as well as other obvious embodiments. Thus, the scope of the invention is to the extent of the annexed claims.

What is claimed:

1. A disposable, rotatable, structure for use in centrifugal separation and washing of liquid-suspended particulate material, having enclosure means for insertion into the rotor of a centrifuge having means adapted and configured for releasably holding said enclosure means with said suspended material therein during rotation thereof about the vertical axis of said enclosure means, comprising in combination:

(a) a plurality of symmetrically shaped, liquid-suspended, particulate material receiving compartments evenly spaced about the periphery of said enclosure means and forming a part of said enclosure means, each of said compartments being symmetrical about an imaginary radial line extending from said vertical axis through the center of said compartment and lying in a plane normal to said vertical axis and being comprised of: (1) at least two opposite side wall portions symmetrical about said imaginary radial line; (2) at least one upper and one lower opposite wall portion symmetrical about said imaginary radial line and said normal plane, each of said opposite wall portions converging towards said imaginary radial line at said periphery of the enclosure and thereby defining a locus of maximum centrifugal force in each of said compartments at the apexes formed by the mutual convergence of said converging wall portions; and (3) an upper and lower annular wall portion within said enclosure, concentric with the center of said enclosure means, symmetrical about said normal plane and spaced apart from each other to define an annular port therebetween in fluid communication with said compartment, said upper and lower annular wall portions intersecting said upper and lower opposite wall portions, respectively;

(b) a fluid distribution means concentrically located within said enclosure means and comprised of a wheel-like disposable member having (1) an inlet port for receiving fluids introduced into said enclosure means; (2) a plurality of outlet ports in fluid communication with a plurality of independent conduit means capable of uniformly and symmetrically dispersing fluids into said compartments, each of said independent conduit means having one end thereof in fluid communication with said locus of maximum centrifugal force, and the other end thereof in fluid communication with one of said outlet ports, each of said independent conduit means extending radially outward from one of said outlet ports into one of said compartments along one of said imaginary radial lines and terminating substantially at said locus; and (3) a concentrically located manifold chamber in fluid communication with said inlet port and said outlet ports, said distribution means defining a first fluid path within said enclosure means; and (c) an upper and a lower plateau, concentric with the axis of rotation, symmetrical about said normal plane, and spaced apart from one another so as to define a passage from the periphery to the central region of the enclosure, the outer periphery of each plateau corresponding to the associated annular wall portion of the enclosure and said passage being in fluid communication with the receiving compartment, via the part formed by the space between the annular wall portions;

(d) a drainage means concentrically located within said enclosure means and comprised of a sump member for removing fluids from said compartments out of said enclosure means, said sump member having an outlet port in fluid communication with the receiving compartments through the passage between the plateaus, said drainage means defining a second fluid path through the enclosure means.

2. A structure as defined in claim 1 wherein said receiving compartments are substantially triangular prismatic shaped.

3. A structure as defined in claim 1 further including two upper and two lower radial wall portions intersecting both said upper and lower annular wall portions of adjacent receiving compartments, thereby forming pentaprismatic shaped receiving compartments.

4. A structure as defined in claim 3 wherein the apex portions of each said compartments are pyramid shaped and the remaining portions of each of said compartments are shaped to resemble the frustum of a pentaprismatic shaped compartment, the vertex of said pyramid shaped portion coinciding with the said locus of maximum centrifugal force within each of said compartments.

5. A structure as defined in claim 4 wherein said pyramid is a right pyramid.

6. A structure as defined in claim 1 wherein there are eight compartments, eight outlet ports associated with said distribution means and eight independent conduit means.

7. A structure as defined in claim 1 wherein said liquid-suspended particulate material is liquid-suspended blood cells, and wherein the volume of each of said compartments is not more than twice the volume of blood cells to be washed at one time within said enclosure means.

8. A structure as defined in claim 1 wherein said upper and lower annular wall portions converge toward the center of said enclosure means forming an angle with said axis sufficient to prevent air from being trapped within said compartments during operation of said apparatus.

9. A structure defined in claim 8 wherein said angle is between about 15° and about 30°.

10. A structure as defined in claim 1 further including a plurality of studs situated within said compartments in contact with and immobilizing the free ends of said independent conduit means extending radially into said compartments.

11. A structure as defined in claim 1 further including a plurality of radial channels within said upper and lower plateaus configured to retain said plurality of independent conduit means therein.

12. A structure as defined in claim 1 wherein said inlet port of said distribution means comprises an inlet nipple for attaching tubing thereto.

13. A structure as defined in claim 1 wherein said exit port of said drainage means extends into an outlet nipple for attaching tubing thereto.

14. A structure as defined in claim 1 wherein said sump member further includes an annular ledge therein and said wheel-like member contains means for centering its location within said enclosure means in said sump member on said ledge.

15. A structure as defined in claim 1 wherein the disposable structure is principally a polymeric material.

16. A structure as defined in claim 15 wherein the structure is composed of a plurality of molded and sealed plastic members which form a unitary structure.

17. A structure as defined in claim 16 wherein the sealing is a heat seal.

18. A structure as defined in claim 16 wherein the plastic is an autoclavable formulation of high impact polyolefin.

19. A structure as defined in claim 16 wherein the plastic is an autoclavable formulation of high impact plastic selected from a polyolefin, polyvinyl chloride, polyvinylidene chloride, polyvinyl acetate, polystyrene, polyacrylate, polyester, polyamide, polysilicone, polycarbonate, polyacetate or butyrate, natural or synthetic rubbers and combinations thereof.

20. A structure as defined in claim 19 wherein said plastic is polypropylene.

21. A structure as defined in claim 19 wherein the plastic is extendable.

* * * * *

UNITED STATES PATENT AND TRADEMARK OFFICE
CERTIFICATE OF CORRECTION

PATENT NO. : 4,157,780
DATED : June 12, 1979
INVENTOR(S) : Edward W. Larrabee

It is certified that error appears in the above-identified patent and that said Letters Patent are hereby corrected as shown below:

Column 9, line 4, after "compartments" insert --and--; line 5, delete "and the" before "apex". Column 10, line 31, insert --leading-- after "therebetween"; line 32, delete "leading"; line 60, insert --3a,-- after "3". Column 12, line 32, delete comma after "92" first instance; line 64, insert --each of -- after "through". Column 13, line 11, delete "transverse".

Signed and Sealed this

Fifteenth Day of January 1980

[SEAL]

Attest:

SIDNEY A. DIAMOND

*Attesting Officer*  *Commissioner of Patents and Trademarks*